(12) United States Patent
Lee et al.

(10) Patent No.: US 10,588,683 B2
(45) Date of Patent: Mar. 17, 2020

(54) METHOD FOR DETERMINING BODY TYPE FOR THERMOTHERAPY DEVICE

(71) Applicant: Ceragem Co., Ltd., Cheonan-si, Chungcheongnam-do (KR)

(72) Inventors: Taek Seung Lee, Chungcheongnam-do (KR); Sang Ui Choi, Seoul (KR); Chang Soo Park, Seongnam-si (KR); Yong Hee Kim, Chungcheongbuk-do (KR); Hea Sung Lee, Chungcheongnam-do (KR)

(73) Assignee: CERAGEM CO., LTD. (KR)

( * ) Notice: Subject to any disclaimer, the term of this patent is extended or adjusted under 35 U.S.C. 154(b) by 776 days.

(21) Appl. No.: 14/354,078

(22) PCT Filed: Oct. 24, 2012

(86) PCT No.: PCT/KR2012/008783
§ 371 (c)(1),
(2) Date: Apr. 24, 2014

(87) PCT Pub. No.: WO2013/062320
PCT Pub. Date: May 2, 2013

(65) Prior Publication Data
US 2014/0277300 A1    Sep. 18, 2014

(30) Foreign Application Priority Data

Oct. 24, 2011 (KR) .......... 10-2011-0109026
Dec. 12, 2011 (KR) .......... 10-2011-0132577

(51) Int. Cl.
*A61B 18/06* (2006.01)
*A61H 39/06* (2006.01)
(Continued)

(52) U.S. Cl.
CPC ............ *A61B 18/06* (2013.01); *A61B 5/1072* (2013.01); *A61B 5/4566* (2013.01); *A61B 5/4854* (2013.01); *A61B 5/684* (2013.01); *A61B 5/6843* (2013.01); *A61B 5/6892* (2013.01); *A61B 5/72* (2013.01); *A61H 15/0078* (2013.01); *A61H 39/06* (2013.01); *A61H 39/08* (2013.01); *A61B 2018/00339* (2013.01); *A61B 2018/00642* (2013.01); *A61F 7/007* (2013.01); *A61F 7/032* (2013.01); *A61H 2015/0028* (2013.01); *A61H 2201/1215* (2013.01); *A61H 2201/1669* (2013.01); *A61H 2201/5064* (2013.01); *A61H 2205/081* (2013.01); *A61H 2230/855* (2013.01)

(58) Field of Classification Search
None
See application file for complete search history.

(56) References Cited

U.S. PATENT DOCUMENTS 4,586,493 A    5/1986    Goodman
6,258,047 B1 *  7/2001   Muramatsu ............ A61B 5/103
                                                    600/594

(Continued)

FOREIGN PATENT DOCUMENTS

CN    201631194    11/2010
JP    07-148221    6/1995
(Continued)

*Primary Examiner* — Sean P Dougherty
*Assistant Examiner* — Benjamin S Melhus
(74) *Attorney, Agent, or Firm* — Riverside Law LLP (57) ABSTRACT

Disclosed herein a method of determining the type of human body in a thermo-therapeutic apparatus. In the method of determining the type of human body in a thermo-therapeutic apparatus, a control unit scans the entire spine of a user by moving a moxibustion device using a horizontal motor, measures the operating current of the horizontal motor, calculates the length of the spine of the human body based on the measured operating current, and precisely determines the positions of the cervical vertebrae, the thoracic vertebrae, the lumbar vertebrae, and the coccyx that form the spine. As a result, acupuncture points suitable for a specific person are calculated and then the calculated acupuncture points are enabled to be used to administer thermotherapy.

3 Claims, 9 Drawing Sheets

(51) Int. Cl.
*A61H 39/08* (2006.01)
*A61H 15/00* (2006.01)
*A61B 5/00* (2006.01)
*A61B 5/107* (2006.01)
A61F 7/03 (2006.01)
A61F 7/00 (2006.01)
A61B 18/00 (2006.01)

(56) References Cited

U.S. PATENT DOCUMENTS

| | | | |
|---|---|---|---|
| 6,832,991 B1* | 12/2004 | Inada | A61H 39/04 |
| | | | 601/100 |
| 2003/0018284 A1* | 1/2003 | Lim | A61H 7/00 |
| | | | 601/98 |
| 2004/0158176 A1 | 8/2004 | Park | |
| 2005/0065580 A1* | 3/2005 | Choi | A61F 7/00 |
| | | | 607/96 |
| 2007/0225624 A1* | 9/2007 | Tsukada | A61H 15/0078 |
| | | | 601/49 |
| 2013/0110007 A1* | 5/2013 | Jeon | A61B 5/4566 |
| | | | 600/594 |

FOREIGN PATENT DOCUMENTS

| | | | |
|---|---|---|---|
| KR | 2002395590000 | 7/2001 | |
| KR | 10-2004-0045106 | 6/2004 | |
| KR | 10-2004-0101947 | 12/2004 | |
| KR | 10-2010-0120756 | 11/2010 | |
| KR | 10-2012-0001602 | 1/2012 | |
| WO | WO 02/069880 | 9/2002 | |
| WO | WO 2011/105179 | 9/2011 | |
| WO | WO 2012002658 A2 * | 1/2012 | A61B 5/1072 |

* cited by examiner

METHOD FOR DETERMINING BODY TYPE FOR THERMOTHERAPY DEVICE

CROSS-REFERENCE TO RELATED APPLICATIONS

This application is the U.S. national phase application filed under 35 U.S.C. § 371 claiming benefit to International Patent Application No. PCT/KR2012/008783, filed on Oct. 24, 2012, which is entitled to priority under 35 U.S.C. § 119(a)-(d) to Korea application nos. 10-2011-0109026, filed Oct. 24, 2011 and 10-2011-0132577, filed Dec. 12, 2011, each of which application is hereby incorporated herein by reference in its entirety.

BACKGROUND OF THE INVENTION

1. Field of the Invention

The present invention relates generally to a method of determining the type of human body in a thermo-therapeutic apparatus and, more particularly, to a method of determining the type of human body in a thermo-therapeutic apparatus, in which a control unit scans the entire spine of a user by moving a moxibustion device using a horizontal motor, measures the operating current of the horizontal motor, calculates the length of the spine of the human body based on the measured operating current, and precisely determines the positions of the cervical vertebrae, the thoracic vertebrae, the lumbar vertebrae, and the coccyx that form the spine, thereby calculating acupuncture points suitable for a specific person and then enabling the calculated acupuncture points to be used to administer thermotherapy.

2. Description of the Related Art

A human has the physiological weakness of becoming relatively easily fatigued because a lot of load is imposed on the spine part in terms of the structure of the body in an upright state, unlike other mammals. In particular, in old age, lots of people have various geriatric diseases or feel physical pain because fatigue accumulates without being relieved because of a significant decrease in immune functionality.

Furthermore, in the recent rapidly spreading Internet environment, even teenagers who are sitting on chairs for a long time in a bad posture and are immersed in the computer experience various diseases and a lot of pain resulting from abnormalities of the spine.

The central nerves of the human body extend to parts of the human body through the spine, and thus major acupuncture points related to not only various geriatric diseases but also the activities of various internal organs, such as the heart, the lungs and the stomach and intestines, are scattered near the spine. In Chinese medicine, in order to enhance the immune functionality, relieve physical pain, and treat and prevent physical pain, chiropractic or moxibustion on spine acupuncture points has been performed for a long time along with acupuncture. Thermo-therapeutic apparatuses focusing on the treatment effects are recently being used in ordinary homes.

In general, thermo-therapeutic apparatuses for treating the diseases of the spine using chiropractic and thermotherapy are configured to stimulate meridian systems and acupuncture points on the spine side while horizontally moving a chiropractic device having a lamp embedded therein. Far-infrared rays emitted from the lamp have an acupuncture effect because they are penetrated deep into the skin, electric heat has a moxibustion effect, and the chiropractic device has an acupuncture effect.

In the conventional thermo-therapeutic apparatus, the width of a pad and the chiropractic device and the chiropractic device are designed based on the spine position of users having an average body type (e.g., height and weight). The conventional thermo-therapeutic apparatus is problematic in that users who do not belong to the average body type and want to receive thermotherapy do not receive proper spine correction and acupuncture effects from the stimulus of the spine-side meridian systems and acupuncture points. In other words, the conventional thermo-therapeutic apparatus focuses on all users having different body types and thus cannot stimulate the spine-side meridian systems and acupuncture points of all the users. The thermo-therapeutic apparatus has the disadvantage of exhibiting its effects on only a very limited set of users.

As described above, in order to determine the spine positions of users having different body types, two signals detected from the spine of the human body must be received, and a variety of research are being conducted into the detection of the two signals.

SUMMARY OF THE INVENTION

Accordingly, the present invention has been made keeping in mind the above problems occurring in the prior art, and an object of the present invention is to provide a method of determining the type of human body in a thermo-therapeutic apparatus, in which a control unit scans the entire spine of a user by moving a moxibustion device using a horizontal motor, measures the operating current of the horizontal motor, calculates the length of the spine of the human body based on the measured operating current, and precisely determines the positions of the cervical vertebrae, the thoracic vertebrae, the lumbar vertebrae, and the coccyx that form the spine, thereby calculating acupuncture points suitable for a specific person and then enabling the calculated acupuncture points to be used to administer thermotherapy.

In order to achieve the above object, the present invention provides a method of determining a type of human body in a thermo-therapeutic apparatus, including step 1 of scanning an entire spine of a user by moving a moxibustion device along a transfer path using a horizontal motor in response to a control signal of a control unit; step 2 of measuring an operating current of the horizontal motor, detecting a first body type determination point in regions of vertebra No. 1 or No. 10 based on a curve of the measured operating current, and detecting a second body type determination point in a region of vertebra No. 24; step 3 of, when there are two peak curves at the second body type determination point, calculating an intersection between extensions of outside slopes of the two peak curves, determining the calculated intersection to be a peak value of the region of vertebra No. 24, and setting the determined peak value as the second body type determination point; step 4 of retrieving standard data of the spine from a database, and calculating an entire length of the spine and a length of each of vertebrae using the standard data and the two body type determination points; and step 5 of the control unit controlling the horizontal motor using the calculated length of each element of the spine as a control value of the horizontal motor.

Additionally, in order to achieve the above object, the present invention provides a method of determining a type of human body in a thermo-therapeutic apparatus, including step 1 of scanning an entire spine of a user by moving a moxibustion device along a transfer path using a horizontal motor in response to a control signal of a control unit; step 2 of measuring an operating current of the horizontal motor, detecting a first body type determination point in a region of vertebra No. 1 or No. 10 based on a curve of the measured operating current, and detecting a second body type determination point in a region of vertebra No. 24; step 3 of, when a peak value is not detected in the region of vertebra No. 24, detecting a single inflection point using a change in a slope of a current curve in the region of vertebra No. 24, determining the single inflection point to be a peak value at a point of vertebra No. 24, and setting the determined peak value as a second body type determination point; step 4 of retrieving standard data of the spine from a database and calculating an entire length of the spine and a length of each of vertebrae using the standard data and the two body type determination points; and step 5 of the control unit controlling the horizontal motor using the calculated length of each element of the spine as a control value of the horizontal motor.

As described above, in the method of determining the type of body in a thermo-therapeutic apparatus according to the present invention, the control unit scans the entire spine of the user by moving a moxibustion device using a horizontal motor, measures the operating current of the horizontal motor, calculates the length of the spine of the human body based on the measured operating current, and precisely determines the positions of the cervical vertebrae, the thoracic vertebrae, the lumbar vertebrae and the coccyx that form the spine. Accordingly, there are advantages in that the thermo-therapeutic apparatus can be controlled based on the body type of each person and moxibustion, acupuncture, and a massage can be precisely controlled at the position of each acupuncture point.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Reference now should be made to the drawings, throughout which the same reference numerals are used to designate the same or similar components.

Embodiments of the present invention will be described in detail below with reference to the accompanying drawings.

Figure 1:
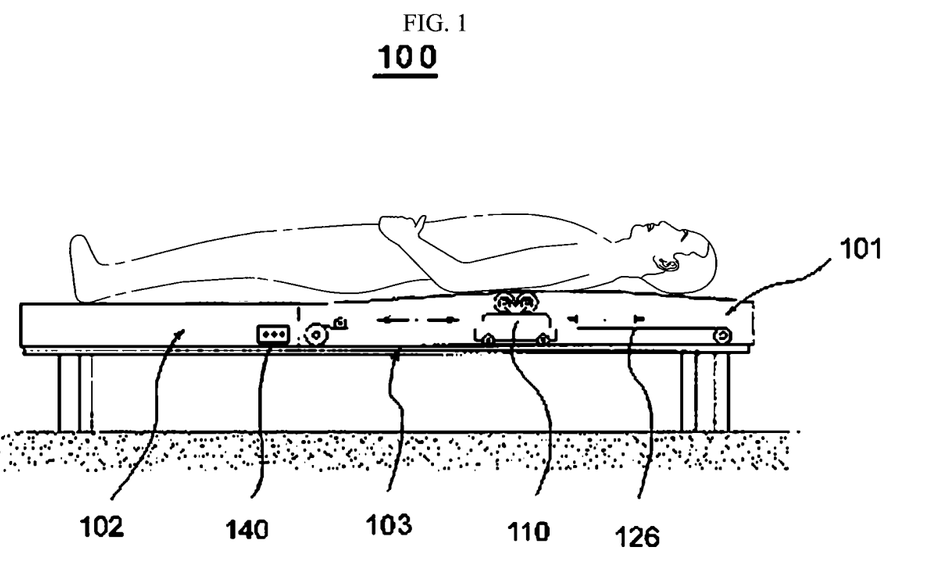
FIG. 1 is a side view of a thermo-therapeutic apparatus according to the present invention.

FIG. 1 shows the configuration of a thermo-therapeutic apparatus according to the present invention. As shown in FIG. 1, the thermo-therapeutic apparatus 100 basically includes a main mat 101 configured to be used for the upper part of the body of a user and the spine of the user, and an auxiliary mat 102 configured to be used for the lower part of the body of the user. The thermo-therapeutic apparatus 100 may further include a mounting unit 103 configured such that the main mat 101 and the auxiliary mat 102 are disposed and supported thereon, if desired. The thermo-therapeutic apparatus 100 is equipped with a moxibustion device 110 configured to provide thermo-therapeutic fomentation and thermo-therapeutic massage effects to the body part of the user (in particular, the back of the user) while moving along the direction of the spine of the user. The moxibustion device 110 provides a user with the thermo-therapeutic fomentation and thermo-therapeutic massage effects using high-temperature heat and far-infrared rays which are generated by means of electrical energy supplied by a power supply unit. The moxibustion device 110 may be of a cap type or of a roller type. The shape of the moxibustion device is not limited to the above types, but may vary in shape and structure. The moxibustion device includes a heat generation unit configured to generate heat using electrical energy and a heating unit configured to be heated by the heat generation unit. In the present embodiment, a lamp or an electric heater is used as the heat generation unit, and a far-infrared radiator, such as jade, is used as the heating unit. However, the heat generation unit and the heating unit are not limited thereto, but may be formed of one of a variety of heating elements and one of materials and substances that can be heated by heat.

The thermo-therapeutic apparatus 100 is equipped with a motor 140 and transfer means 126 so that the moxibustion device 110 can reciprocate within the thermo-therapeutic apparatus. The motor 140 is supplied with and rotated by electrical energy. The transfer means 126 is connected to the motor 140, and transfers the rotary power of the motor 140 while the motor 140 is rotating, thereby moving the moxibustion device. The transfer means 126 is connected to the moxibustion device 110, and is used to move the moxibustion device 110 forward and backward (i.e., in one direction and in the opposite direction) when the motor 140 is rotated forward or backward. One of a conveyer belt, a transfer chain and a transfer rope may be selectively used as the transfer means 126. One of a variety of types of means for transferring an object using the driving force of the motor may be used.

The thermo-therapeutic apparatus 100 includes a control unit for controlling the operation of the thermo-therapeutic apparatus, an input unit for receiving a manipulation signal from a user and providing the manipulation signal to the control unit, and memory for storing the received information. The control unit controls the period, range and time in which the various parts of the thermo-therapeutic apparatus operate, and operates or stops the various parts in accordance with pre-programmed information. In the present embodiment, the control unit may be a single control chip or element or a plurality of control chips or elements mounted on a single PCB or a plurality of PCBs. The memory stores information about diseases and massages and information received using the input unit. The user may input the required information using the input unit while holding the input unit in his or her hand. Here, the input unit may be configured in a wired or wireless manner.

Figure 2:
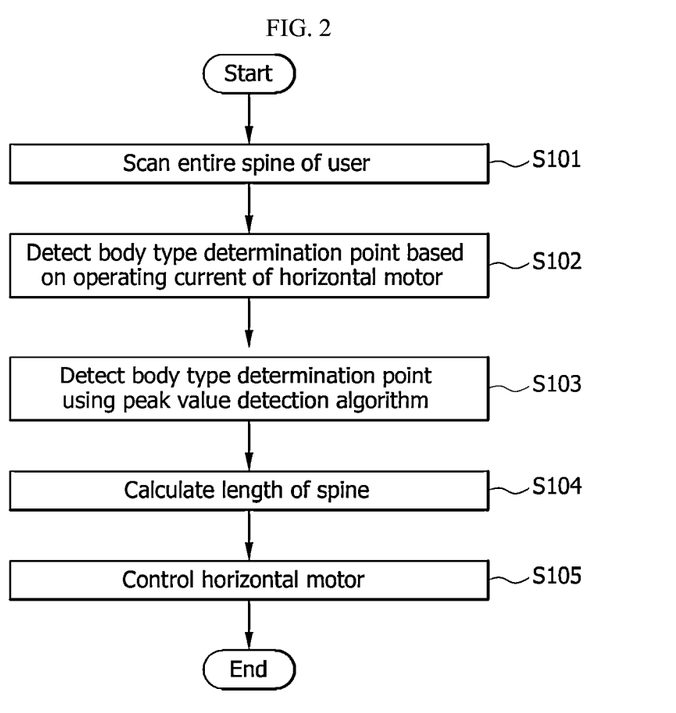
FIG. 2 is a flowchart illustrating a method of determining the type of human body according to the present invention.

FIG. 2 is a flowchart illustrating a method of determining the type of human body according to the present invention.

Figure 3A:
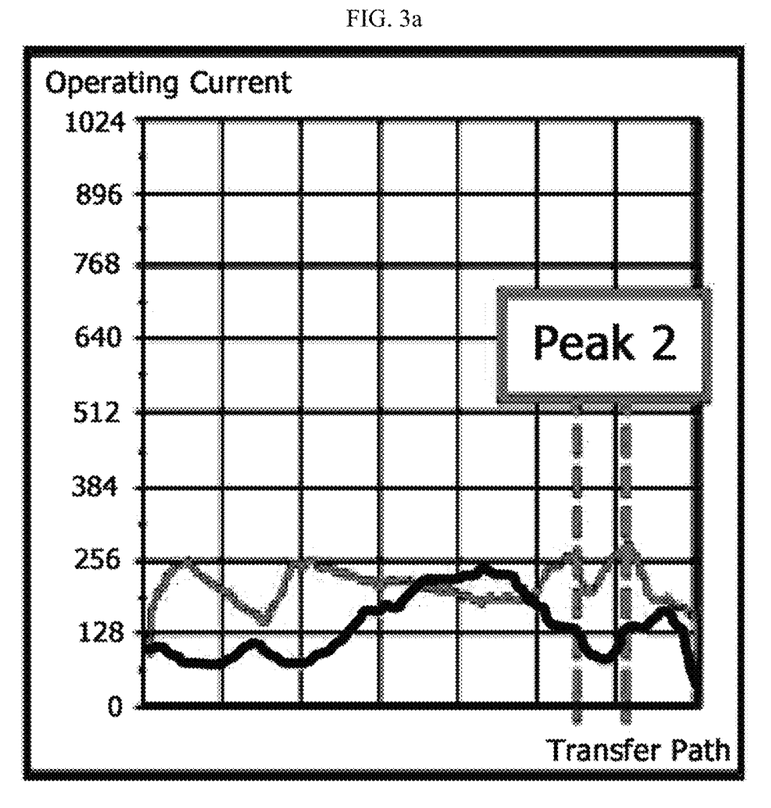
FIGS. 3A and 3B are diagrams showing an embodiment of the current curve of a horizontal motor according to the present invention.
Figure 3B:
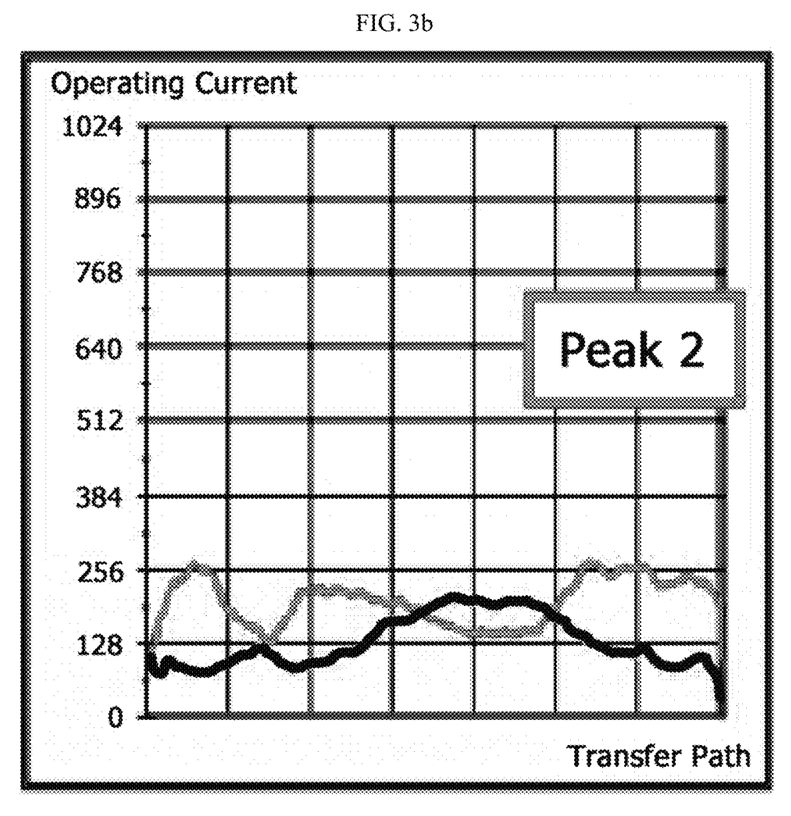
Figure 4A:
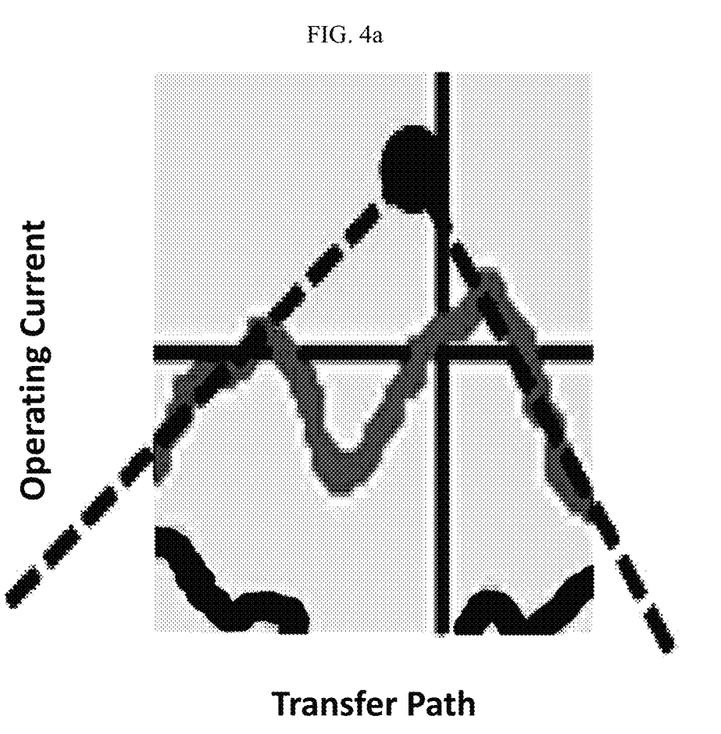
FIG. 4A is a diagram showing a method of calculating a peak value when the number of peaks 2 are two peaks according to the present invention.
Figure 4B:
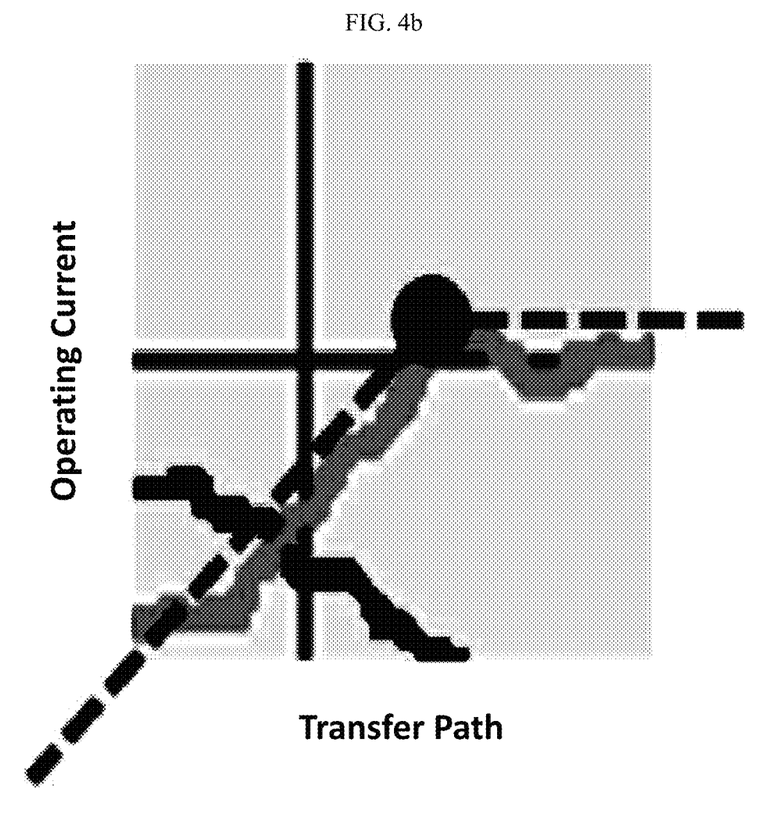
FIG. 4B is a diagram showing a method of calculating a peak value when the number of peaks 2 is zero according to the present invention.

First, the horizontal motor moves the moxibustion device along a transfer path in response to the control signal of the control unit, the entire spine of a user is scanned at step S101, and the operating current of the horizontal motor is measured. Body type determination points are detected based on the curve of the measured operating current at step S102. In order to determine the spine positions of all users having different body types, two body type determination points must be detected from the spine of the human body of each user. A first body type determination point is detected in the region of vertebra No. 10. That is, a position at which a first peak value is detected is the position of vertebra No. 10, and thus becomes the first body type determination point, in term of the structure of the spine. Furthermore, when the moxibustion device starts moving from the position of vertebra No. 1, the position of vertebra No. 1 becomes a body type determination point because the position of the spine may be determined, even if a peak value is not detected. A second body type determination point is detected in the region of vertebra No. 24. However, if the moxibustion device is tilted when the moxibustion device passes over the pelvic bone, two peak values are detected in the region of vertebra No. 24 because the motor current suddenly changes (see FIG. 3A). Furthermore, if a phenomenon in which the body of a user is pushed downwards along with the moxibustion device occurs when the moxibustion device passes over the pelvic bone, a peak value is not detected in the region of vertebra No. 24 (see FIG. 3B). If a peak value is not detected in the region of vertebra No. 24 or two peak values are detected in the region of vertebra No. 24 as described above because the moxibustion device does not normally scan the spine of the user, the second body type determination point may be calculated using a peak value detection algorithm at step S103. If two peak values are detected in the region of vertebra No. 24, the intersection between the extensions of the outside slopes of the two peak curves is determined to be a peak value (see FIG. 4A). The determined peak value is the second body type determination point. Furthermore, if a peak value is not detected in the region of vertebra No. 24, a single inflection point is detected based on a change in the slope of a current curve and determined to be a peak value (see FIG. 4B). The determined peak value is the second body type determination point.

Thereafter, after the body type determination points have been determined in the regions of vertebrae Nos. 1 and 24 or the regions of vertebrae Nos. 10 and 24, the length of the spine is calculated using standard data of the spine based on the determined body type determination points at step S104. After the entire length of the spine has been calculated, the length of each of the cervical vertebrae, the thoracic vertebrae, the lumbar vertebrae, and the coccyx, or the length of each of the vertebrae No. 1 to No. 30 is calculated using standard data of the spine stored in the database. The database stores the distance between two peak values when the two peak values are detected, the standard length of each of the cervical vertebrae, the thoracic vertebrae, the lumbar vertebrae, and the coccyx and the standard length of each of the vertebrae No. 1 to No. 30. Accordingly, it is possible to calculate the length of each element of the spine of each actual user using the proportionate relationships between the standard lengths.

After the length of each element of the spine has been calculated, the calculated length of each element of the spine becomes a control value of the horizontal motor. The control unit operates the horizontal motor using control values of the horizontal motor, so that the thermo-therapeutic apparatus is operated based on the body type of a user along the spine of the user at step S105.

Figure 5:
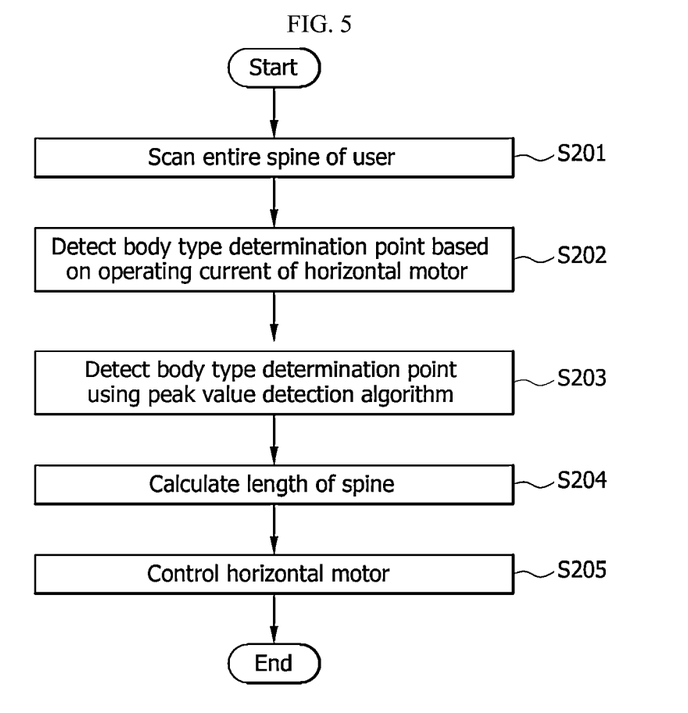
FIG. 5 is a flowchart illustrating a method of determining the type of human body according to the present invention.

FIG. 5 is a flowchart illustrating a method of determining the type of human body according to another embodiment of the present invention.

Figure 6A:
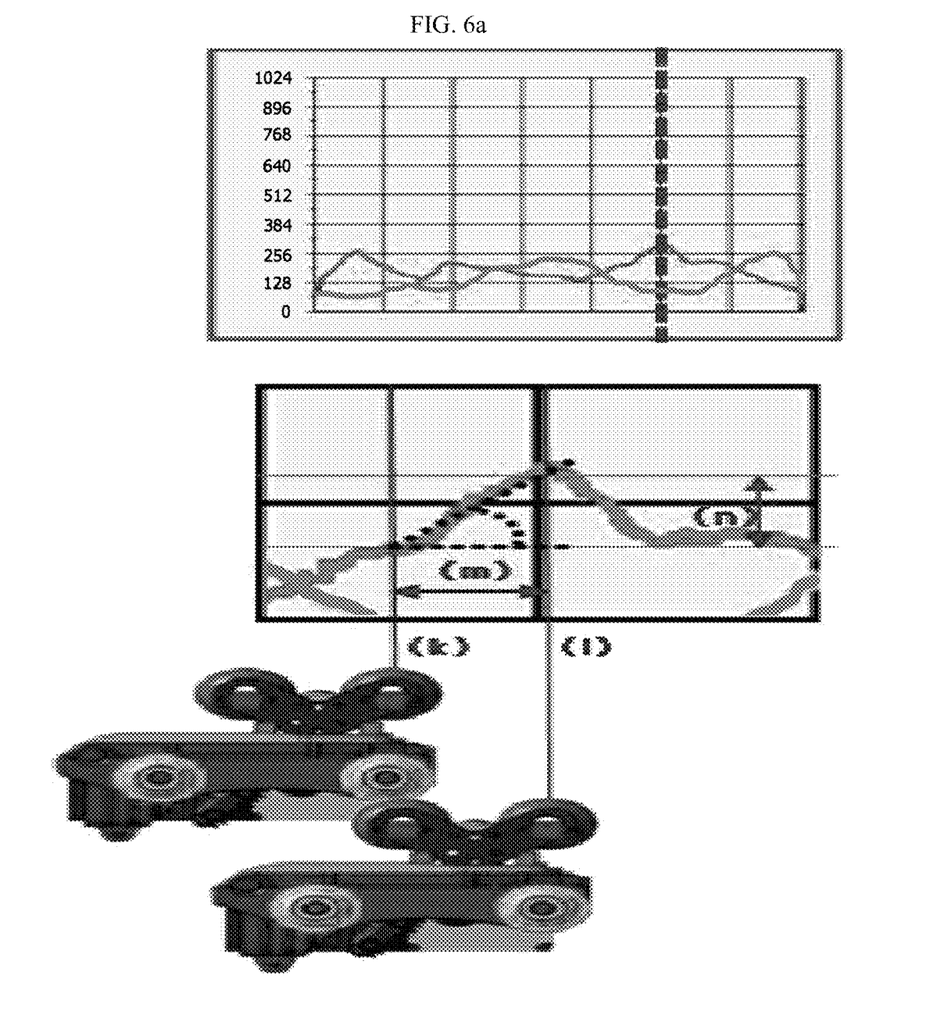
FIGS. 6A and 6B are diagrams showing an embodiment of the current curve of the horizontal motor according to the present invention.
Figure 6B:
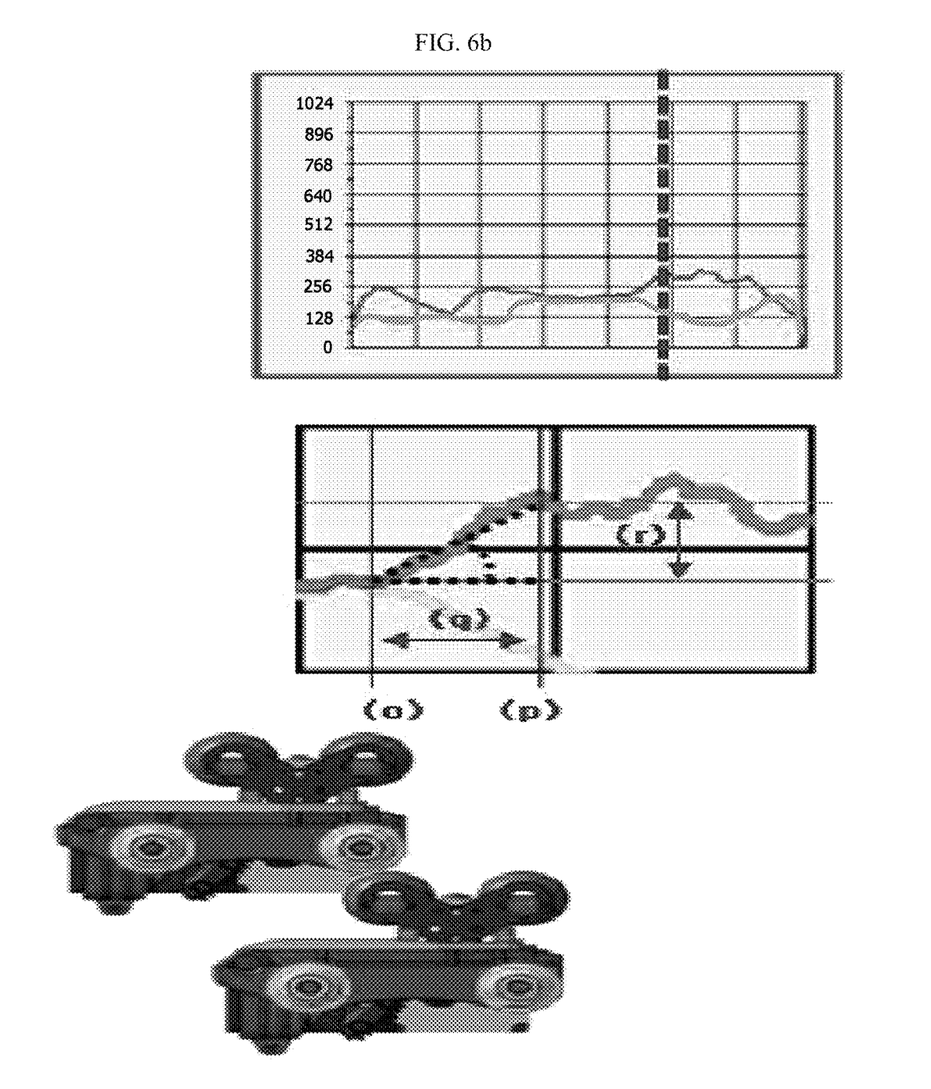

First, the horizontal motor moves the moxibustion device along a transfer path in response to the control signal of the control unit, the entire spine of the user is scanned at step S201, and the operating current of the horizontal motor is measured. Body type determination points are detected based on the curve of the measured operating current at step S202. In order to determine the spine positions of all users having different body types, two body type determination points must be detected from the spine of the human body of each user. A first body type determination point is detected in the region of vertebra No. 10. That is, a position where a first peak value is detected is the position of vertebra No. 10 and thus becomes the first body type determination, in terms of the structure of the spine. Furthermore, when the moxibustion device starts moving from the position of vertebra No. 1, the position of vertebra No. 1 becomes a body type determination point because the position of the spine can be determined, even if a peak value is not detected. A second body type determination point is detected in the region of vertebra No. 24. However, if the moxibustion device is tilted when the moxibustion device passes over the pelvic bone or a phenomenon in which the body of a user is pushed downwards along with the moxibustion device occurs, the region of vertebra No. 24 cannot be precisely determined because a motor current suddenly changes. If the second body type determination point is not detected as described above because the moxibustion device cannot normally scan the spine of the user, a peak value may be calculated using a peak value detection algorithm at step S203. The peak value detection algorithm measures the change in the difference between the operating current of the horizontal motor in a current position of the moxibustion device and the operating current of the horizontal motor at a previous position of the moxibustion device when the moxibustion device moves, determines the maximum value to be a peak value, and sets the determined maximum as the second body type determination point. Here, the previous position refers to a position which precedes the current one by the distance between the front of the moxibustion device and the rear of the moxibustion device and at which the moxibustion device has already arrived. This will now be described in detail with reference to FIG. 6A. Referring to FIG. 6A, the horizontal axis of the graph indicates positions across which the moxibustion device moves along the spine, and the vertical axis thereof indicates operating currents of the horizontal motor of the moxibustion device. Here, assuming that the current position of the moxibustion device is (l), the previous position of the moxibustion device is (k) corresponding to a position preceding the current one by the distance between the front of the moxibustion device and the rear of the moxibustion device. The distance value (m) indicates the distance between the front of the moxibustion device and the rear of the moxibustion device, and a position preceding the current one by the distance value (m) is the previous position. Furthermore, (n) indicates the difference between the operating currents of the horizontal motor at the current position (l) and the previous position (k). Accordingly, while the moxibustion device is moving along the spine, the difference (n) between the operating currents of the horizontal motor in each position is calculated. The maximum value in this difference is a peak value, and the position of the moxibustion device at the maximum value is the position of vertebra No. 24. In this case, the position of vertebra No. 24 becomes the second body type determination point. FIG. 6B shows another embodiment of the present invention. Here, assuming that a current position of the moxibustion device is (p), the previous position of the moxibustion device is (o) corresponding to a position previous by the distance (q) between the front of the moxibustion device and the rear of the moxibustion device. (r) indicates the difference between the operating currents of the horizontal motor at the current position (l) and the previous position (k). Accordingly, the difference (r) between the operating currents of the horizontal motor at the respective positions is calculated while the moxibustion device is moving along the spine. The value at which the difference (r) is maximum is a peak value, and position (p) of the moxibustion device at the peak value is the position of vertebra No. 24. Here, the position of vertebra No. 24 becomes the second body type determination point.

Thereafter, after the body type determination points have been determined in the regions of vertebrae Nos. 1 and 24 or the regions of vertebrae Nos. 10 and 24, the length of the spine is calculated using standard data of the spine based on the determined body type determination points at step S204. After the entire length of the spine has been calculated, the length of each of the cervical vertebrae, the thoracic vertebrae, the lumbar vertebrae, and the coccyx, or the length of each of the vertebrae No. 1 to No. 30 is calculated using standard data of the spine stored in the database. The database stores the distance between two body type determination points when the two body type determination points are detected, the standard length of each of the cervical vertebrae, the thoracic vertebrae, the lumbar vertebrae, and the coccyx and the standard length of each of the vertebrae No. 1 to No. 30. Accordingly, the length of each element of the spine of each user can be calculated using the proportionate relationships between the standard lengths.

After the length of each element of the spine has been calculated, the calculated length of the element of the spine becomes a control value of the horizontal motor. The control unit operates the horizontal motor using control values of the horizontal motor, so that thermo-therapeutic apparatus is operated based on the body type of the user along the spine of the user at step S205.

What is claimed is:

1. A method of accurately stimulating the spinal meridian systems and acupuncture points of a patient using a thermo-therapeutic apparatus, comprising:
    step 1 of a moxibustion device applying a massage pressure against an entire length of a patient's spine using a horizontal motor in response to a control signal of a control unit, the moxibustion device having a front and a rear separated by a distance in-between;
    step 2 of measuring an operating current of the horizontal motor, and recording a first peak reading as a first body type determination point in a region of vertebra No. 1 or No. 10;
    step 3 of measuring a change in difference between an operating current of the horizontal motor at each position of the moxibustion device and an operating current of the horizontal motor at a previous position of the moxibustion device in a region of vertebrae No. 24 when the operating current suddenly changes, wherein the previous position refers to a position which precedes a current position by the distance between the front of the moxibustion device and the rear of the moxibustion device and at which the moxibustion device has already arrived, and calculating a maximum value to be a second peak reading as a second body type determination point;
    step 4 of retrieving standard data of the spine from a database and calculating the length of the patient's spine and a length of each of the patient's vertebrae based on the standard data and the two body type determination points to identify an actual location of each of the patient's vertebrae; and
    step 5 of the control unit controlling the horizontal motor to perform thermo-therapeutic fomentation and thermo-therapeutic massages at the actual location of each of the patient's vertebrae using the calculated lengths of the patient's spine and vertebrae.

2. The method as set forth in claim 1, wherein step 3 comprises:
    step 3-1 of measuring an operating current of the horizontal motor at each position of the spine when the moxibustion device moves along the spine;
    step 3-2 of calculating a change in the difference between the operating current of the horizontal motor at each position of the moxibustion device and the operating current of the horizontal motor at a previous position of the moxibustion device; and
    step 3-3 of calculating a value at which the difference (r) is maximum to be a peak value, determining a position of the moxibustion device at the peak value to be a position of vertebra No. 24, and setting the position of vertebra No. 24 as the second body type determination point.

3. The method as set forth in claim 1 or 2, wherein the standard data includes a distance between the two body type determination points when the two body type determination points are detected; a standard length of each cervical vertebrae, thoracic vertebrae, lumbar vertebrae, and coccyx; and a standard length of each of the vertebrae No. 1 to No. 30.

* * * * *